US012763208B2

(12) United States Patent
(10) Patent No.: US 12,763,208 B2
(45) Date of Patent: Oct. 13, 2026

Chen et al.

(54) SYSTEM AND METHOD TO DETECT AND ADDRESS OVERWEIGH PERCEIVED BY A SUBJECT IN A SALIENT SITUATION

(71) Applicant: TOYOTA RESEARCH INSTITUTE, INC., Los Altos, CA (US)

(72) Inventors: Yin-Ying Chen, San Jose, CA (US); Totte Harinen, San Francisco, CA (US); David Ayman Shamma, San Francisco, CA (US); Emily S. Sumner, Mountain View, CA (US)

(73) Assignee: TOYOTA RESEARCH INSTITUTE, INC., Los Altos, CA (US)

( * ) Notice: Subject to any disclaimer, the term of this patent is extended or adjusted under 35 U.S.C. 154(b) by 1303 days.

(21) Appl. No.: 17/581,731

(22) Filed: Jan. 21, 2022

(65) Prior Publication Data

US 2023/0290500 A1 Sep. 14, 2023

(51) Int. Cl.

| | |
|---|---|
| ***G16H 50/20*** | (2018.01) |
| ***A61B 5/00*** | (2006.01) |
| ***A61B 5/16*** | (2006.01) |
| ***G06Q 30/0201*** | (2023.01) |
| ***G16H 10/20*** | (2018.01) |
| ***G16H 10/60*** | (2018.01) |
| ***G16H 20/70*** | (2018.01) |

(52) U.S. Cl.

CPC ............. *G16H 50/20* (2018.01); *A61B 5/165* (2013.01); *A61B 5/7264* (2013.01); *G06Q 30/0201* (2013.01); *G16H 10/20* (2018.01); *G16H 10/60* (2018.01); *G16H 20/70* (2018.01)

(58) Field of Classification Search

CPC ........ G16H 50/20; G16H 10/20; G16H 10/60; G16H 20/70; G16H 50/30; A61B 5/165; A61B 5/7264; G06Q 30/0201

See application file for complete search history.

(56) References Cited

U.S. PATENT DOCUMENTS

| | | | | |
|---|---|---|---|---|
| 9,569,467 | B1 | 2/2017 | Schechter et al. | |
| 10,226,209 | B2 | 3/2019 | Girouard | |
| 10,762,514 | B1 | 9/2020 | O'Toole | |
| 10,980,469 | B2 * | 4/2021 | Girouard | A61B 5/4094 |
| 11,257,574 | B1 * | 2/2022 | Boussios | G06N 20/00 |
| 11,475,335 | B2 * | 10/2022 | Routray | G06N 20/00 |
| 2018/0289310 | A1 * | 10/2018 | Girouard | A61B 5/7282 |
| 2022/0358146 | A1 * | 11/2022 | Xu | G06F 16/258 |
| 2022/0392642 | A1 * | 12/2022 | Dasi | G16H 50/50 |

FOREIGN PATENT DOCUMENTS

| | | |
|---|---|---|
| CN | 111127059 A | 5/2020 |

* cited by examiner

*Primary Examiner* — Catherine T. Rastovski
*Assistant Examiner* — Michael J Singletary
(74) *Attorney, Agent, or Firm* — SEYFARTH SHAW LLP

(57) ABSTRACT

A method for information overweight detection and intervention is described. The method includes training a statistical model to classify salient information that may be overweight by individuals to provide a trained statistical model. The method also includes collecting data from a user about the salient information experienced by the user or to which the user is exposed. The method further includes analyzing the salient information using the trained statistical model to identify and classify the salient information that the user may overweight to identify overweight information. The method also includes presenting one or more interventions to the user to prevent the user from overweighting the identified overweight information.

20 Claims, 6 Drawing Sheets

SYSTEM AND METHOD TO DETECT AND ADDRESS OVERWEIGH PERCEIVED BY A SUBJECT IN A SALIENT SITUATION

BACKGROUND

Field

Certain aspects of the present disclosure generally relate to machine learning and, more particularly, to a system and method for detecting and addressing overweighing of salient information to which a user is exposed.

Background

As the public experiences the world, either in-person, online, or through periodicals, they may be exposed to significant events. In particular, when people are exposed to rare but salient examples, or emotional experiences (e.g., an electric vehicle battery explosion), they may overweight the likelihood of such events occurring in the future. In particular, if a single event is repeatedly portrayed in the media, people may think that such an event occurs more often than they actually occur in reality. In addition, if a single salient but rare event happens to a particular person (e.g., an electric vehicle (EV) battery explosion), that individual may overweight the likelihood of a similar event occurring in the future.

Unfortunately, people may overweight the importance of salient events and may have excessive fear or anxiety about a similar, salient event occurring in the future that is disproportionate to its actual likelihood of occurrence. A method for protecting people from inappropriately overweighting information, is desired.

SUMMARY

A method for information overweight detection and intervention is described. The method includes training a statistical model to classify salient information that may be overweight by individuals to provide a trained statistical model. The method also includes collecting data from a user about the salient information experienced by the user or to which the user is exposed. The method further includes analyzing the salient information using the trained statistical model to identify and classify the salient information that the user may overweight to identify overweight information. The method also includes presenting one or more interventions to the user to prevent the user from overweighting the identified overweight information.

A non-transitory computer-readable medium having program code recorded thereon for information overweight detection and intervention is described. The program code is executed by a processor. The non-transitory computer-readable medium includes program code to train a statistical model to classify salient information that may be overweight by individuals to provide a trained statistical model. The non-transitory computer-readable medium also includes program code to collect data from a user about the salient information experienced by the user or to which the user is exposed. The non-transitory computer-readable medium further includes program code to analyze the salient information using the trained statistical model to identify and classify the salient information that the user may overweight to identify overweight information. The non-transitory computer-readable medium also includes program code to present one or more interventions to the user to prevent the user from overweighting the identified overweight information.

A system for information overweight detection and intervention is described. The system includes an overweight information training module to train a statistical model to classify salient information that may be overweight by individuals to provide a trained statistical model. The system also includes a data collection module to collect data from a user about the salient information experienced by the user or to which the user is exposed. The system further includes an overweight information detection model to analyze the salient information using the trained statistical model to identify and classify the salient information that the user may overweight to identify overweight information. The system also includes an intervention presentation and tracking model to present one or more interventions to the user to prevent the user from overweighting the identified overweight information.

This has outlined, rather broadly, the features and technical advantages of the present disclosure in order that the detailed description that follows may be better understood. Additional features and advantages of the present disclosure will be described below. It should be appreciated by those skilled in the art that this present disclosure may be readily utilized as a basis for modifying or designing other structures for carrying out the same purposes of the present disclosure. It should also be realized by those skilled in the art that such equivalent constructions do not depart from the teachings of the present disclosure as set forth in the appended claims. The novel features, which are believed to be characteristic of the present disclosure, both as to its organization and method of operation, together with further objects and advantages, will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

The features, nature, and advantages of the present disclosure will become more apparent from the detailed description set forth below when taken in conjunction with the drawings in which like reference characters identify correspondingly throughout.

DETAILED DESCRIPTION

Figure 1:
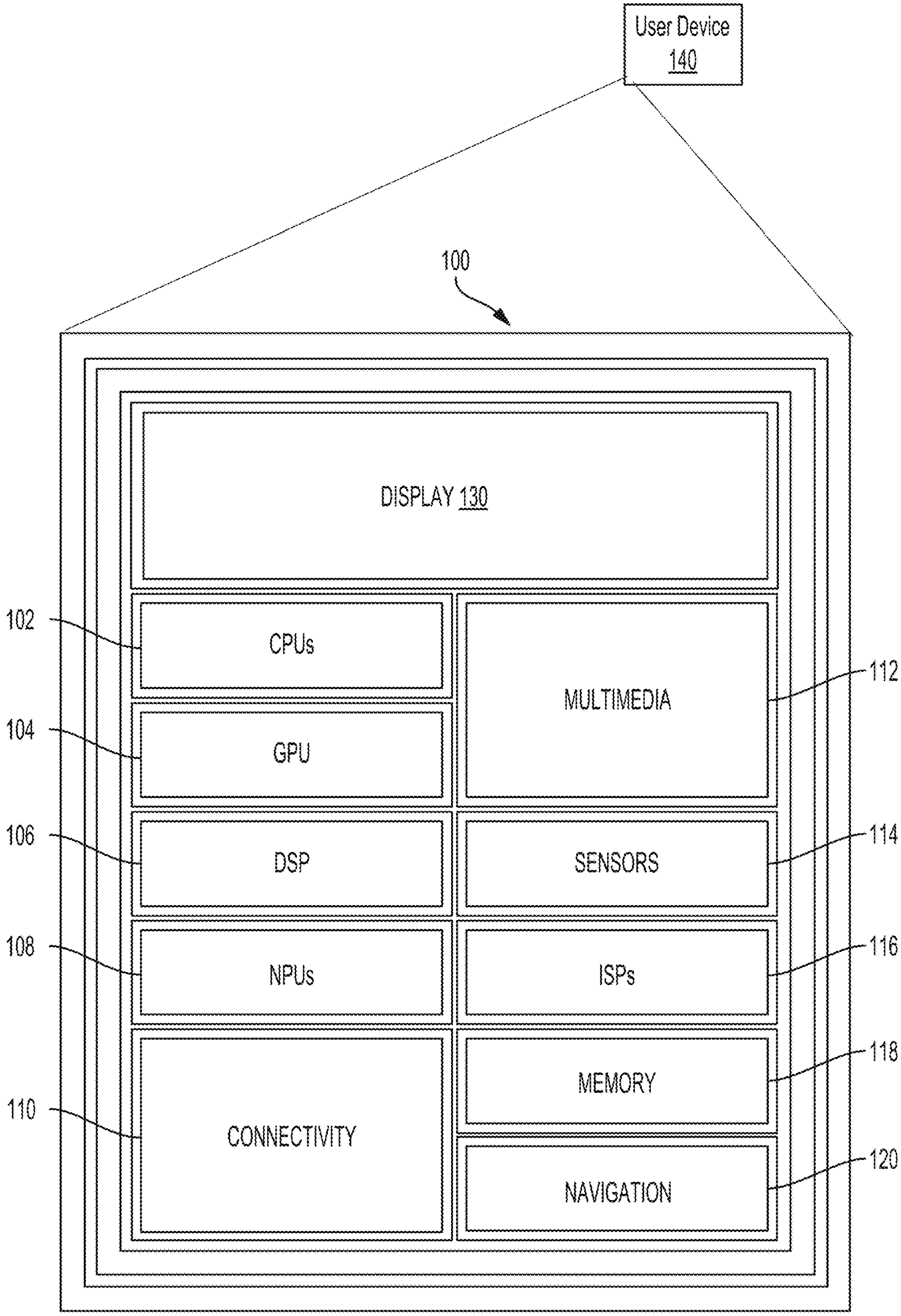
FIG. 1 illustrates an example implementation of designing a neural network using a system-on-a-chip (SOC) of an information overweight detection and intervention system, in accordance with aspects of the present disclosure.

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. It will be apparent to those skilled in the art, however, that these concepts may be practiced without these specific details. In some instances, well-known structures and components are shown in block diagram form in order to avoid obscuring such concepts.

Based on the teachings, one skilled in the art should appreciate that the scope of the present disclosure is intended to cover any aspect of the present disclosure, whether implemented independently of or combined with any other aspect of the present disclosure. For example, an apparatus may be implemented or a method may be practiced using any number of the aspects set forth. In addition, the scope of the present disclosure is intended to cover such an apparatus or method practiced using other structure, functionality, or structure and functionality in addition to, or other than the various aspects of the present disclosure set forth. It should be understood that any aspect of the present disclosure disclosed may be embodied by one or more elements of a claim.

Although particular aspects are described herein, many variations and permutations of these aspects fall within the scope of the present disclosure. Although some benefits and advantages of the preferred aspects are mentioned, the scope of the present disclosure is not intended to be limited to particular benefits, uses, or objectives. Rather, aspects of the present disclosure are intended to be broadly applicable to different technologies, system configurations, networks, and protocols, some of which are illustrated by way of example in the figures and in the following description of the preferred aspects. The detailed description and drawings are merely illustrative of the present disclosure, rather than limiting the scope of the present disclosure being defined by the appended claims and equivalents thereof.

As the public experiences the world, either in-person, online, or through periodicals, they may be exposed to significant events. In particular, when people are exposed to rare but salient examples, or emotional experiences (e.g., an electric vehicle battery explosion), they may overweight the likelihood of such events occurring in the future. In particular, if a single event is repeatedly portrayed in the media, people may think that such an event occurs more often than they actually occur in reality. In addition, if a single salient but rare event happens to a particular person (e.g., an electric vehicle (EV) battery explosion), that individual may overweight the likelihood of a similar event occurring in the future.

Unfortunately, people may overweight the importance of salient events and may have excessive fear or anxiety about a similar, salient event occurring in the future that is disproportionate to its actual likelihood of occurrence. Some aspects of the present disclosure are directed to a method for protecting people from inappropriately overweighting information. Some aspects of the present disclosure ameliorate overweighting the importance of salient events using a machine learning model trained on a set of past overweight events from the user as well as the broader population to provide an intervention strategy for protecting the user from inappropriately overweighting salient events.

Some aspects of the present disclosure are to protect people from inappropriately overweighting information by collecting data of events that an individual may potentially overweight. The data may be collected by a variety of means including self-reporting, browser history, physiological signals (e.g., heart rate), video, and speech. The system may then aggregate the collected data from the individual and from the broader population. A model may then be trained to determine the type of overweighting likely to occur using either supervised learning (based on collected data from the population) or unsupervised learning.

In some aspects of the present disclosure, a statistical model is trained to analyze data collected from an individual to determine and classify how the individual is likely to overweight certain events. In response to predicting overweighting of a salient event, an information overweight detection and intervention system may suggest interventions to prevent the individual from overweighting the salient event based on the classification of the salient event. For example, interventions may include presenting actual statistical data about the type of event, instructing the individual on how to avoid situations that raise fear or anxiety, and the like. The interventions may be presented to the user and the information overweight detection and intervention system may then track the user's reactions to the interventions and continuously revise the suggested interventions.

FIG. 1 illustrates an example implementation of the aforementioned system and method for an information overweight detection and intervention system using a system-on-a-chip (SOC) 100, according to aspects of the present disclosure. The SOC 100 may include a single processor or multi-core processors (e.g., a central processing unit (CPU) 102), in accordance with certain aspects of the present disclosure. Variables (e.g., neural signals and synaptic weights), system parameters associated with a computational device (e.g., neural network with weights), delays, frequency bin information, and task information may be stored in a memory block. The memory block may be associated with a neural processing unit (NPU) 108, a CPU 102, a graphics processing unit (GPU) 104, a digital signal processor (DSP) 106, a dedicated memory block 118, or may be distributed across multiple blocks. Instructions executed at a processor (e.g., CPU 102) may be loaded from a program memory associated with the CPU 102 or may be loaded from the dedicated memory block 118.

The SOC 100 may also include additional processing blocks configured to perform specific functions, such as the GPU 104, the DSP 106, and a connectivity block 110, which may include fourth generation long term evolution (4G LTE) connectivity, unlicensed Wi-Fi connectivity, USB connectivity, Bluetooth® connectivity, and the like. In addition, a multimedia processor 112 in combination with a display 130 may, for example, select a control action, according to the display 130 illustrating a view of a user device.

In some aspects, the NPU 108 may be implemented in the CPU 102, DSP 106, and/or GPU 104. The SOC 100 may further include a sensor processor 114, image signal processors (ISPs) 116, and/or navigation 120, which may, for instance, include a global positioning system. The SOC 100 may be based on an Advanced Risk Machine (ARM) instruction set or the like. In another aspect of the present disclosure, the SOC 100 may be a server computer in communication with a user device 140. In this arrangement, the user device 140 may include a processor and other features of the SOC 100.

In this aspect of the present disclosure, instructions loaded into a processor (e.g., CPU 102) or the NPU 108 of the user device 140 may include code to train a statistical model to classify salient information that may be overweight by individuals to provide a trained statistical model. The instructions loaded into a processor (e.g., CPU 102) may also include code to collect data from a user about salient information experienced by the user or to which the user is exposed. The instructions loaded into a processor (e.g., CPU 102) may also include code to analyze the salient information using the trained statistical model to identify and classify salient information that the user may overweight to identify overweight information. The instructions loaded into a processor (e.g., CPU 102) may also include code to present one or more interventions to the user to prevent the user from overweighting the identified overweight information.

Figure 2:
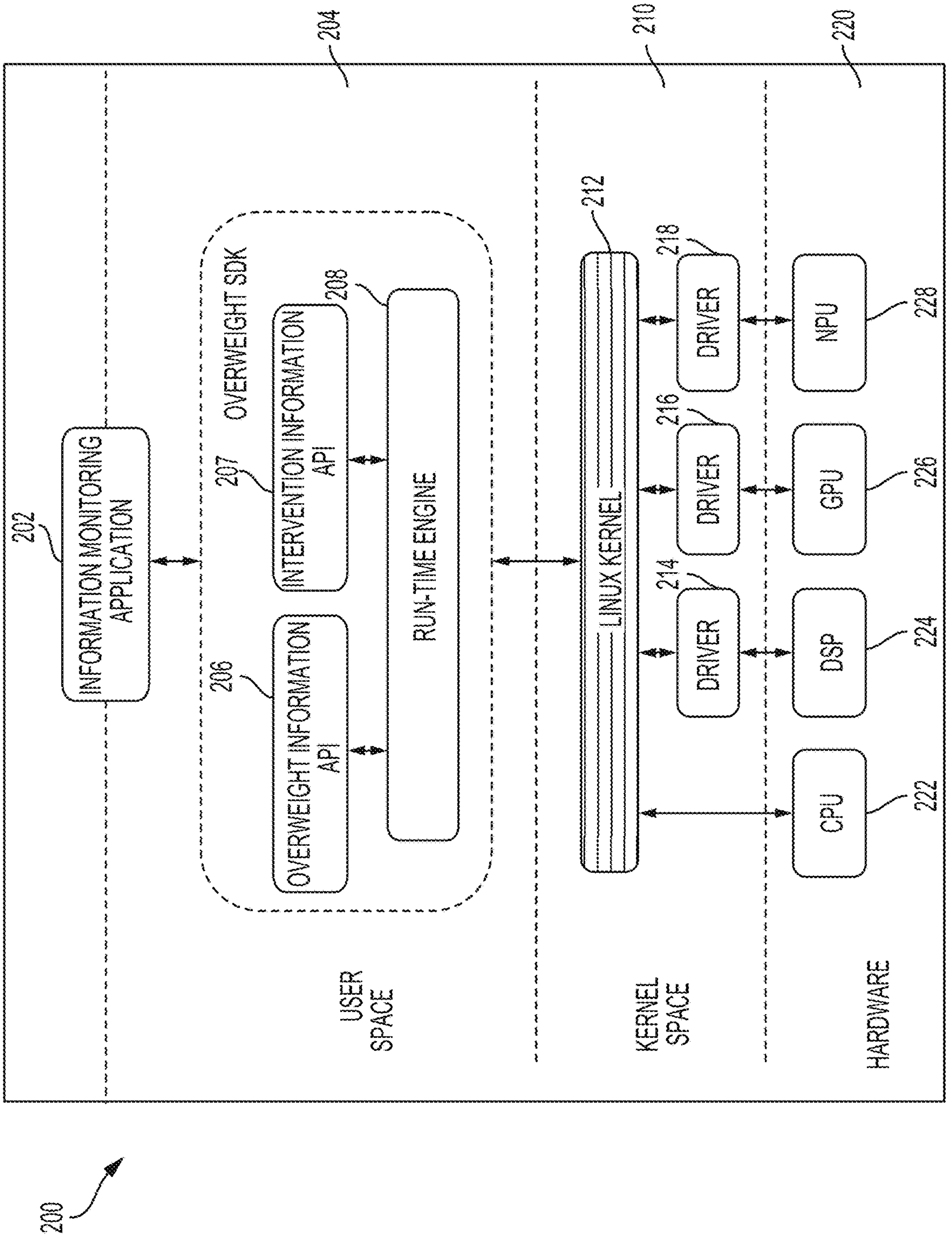
FIG. 2 is a block diagram illustrating an exemplary software architecture that may modularize artificial intelligence (AI) functions for an information overweight detection and intervention system, according to aspects of the present disclosure.

FIG. 2 is a block diagram illustrating a software architecture 200 that may modularize artificial intelligence (AI) functions for an information overweight detection and intervention system, according to aspects of the present disclosure. Using the architecture, an information monitoring application 202 may be designed such that it may cause various processing blocks of an SOC 220 (for example a CPU 222, a DSP 224, a GPU 226, and/or an NPU 228) to perform supporting computations during run-time operation of the information monitoring application 202. FIG. 2 describes the software architecture 200 for information overweight detection and intervention. It should be recognized that the information overweight detection and intervention system is not limited to in-person events. According to aspects of the present disclosure, the information overweight detection and intervention functionality is applicable to any type of event or user activity.

The information monitoring application 202 may be configured to call functions defined in a user space 204 that may, for example, provide for user activity and information monitoring services. The information monitoring application 202 may make a request for compiled program code associated with a library defined in an overweight information application programming interface (API) 206. The overweight information API 206 is configured to analyze salient information experienced by the user or to which the user is exposed using a trained statistical model to identify and classify salient information that the user may overweight to identify overweight information. In response, compiled code of an intervention information API 207 is configured to present one or more interventions to the user to prevent the user from overweighting the identified overweight information.

A run-time engine 208, which may be compiled code of a run-time framework, may be further accessible to the information monitoring application 202. The information monitoring application 202 may cause the run-time engine 208, for example, to take actions for providing interventions in response to identified overweight information. In response to detection of overweight salient information, the run-time engine 208 may in turn send a signal to an operating system 210, such as a Linux Kernel 212, running on the SOC 220. FIG. 2 illustrates the Linux Kernel 212 as software architecture for information overweight detection and intervention. It should be recognized, however, that aspects of the present disclosure are not limited to this exemplary software architecture. For example, other kernels may provide the software architecture to support information overweight detection and intervention functionality.

The operating system 210, in turn, may cause a computation to be performed on the CPU 222, the DSP 224, the GPU 226, the NPU 228, or some combination thereof. The CPU 222 may be accessed directly by the operating system 210, and other processing blocks may be accessed through a driver, such as drivers 214-218 for the DSP 224, for the GPU 226, or for the NPU 228. In the illustrated example, the deep neural network may be configured to run on a combination of processing blocks, such as the CPU 222 and the GPU 226, or may be run on the NPU 228, if present.

As the individuals experiences the world, either in-person, online, or through periodicals, they may be exposed to significant events. In particular, when Individuals are exposed to rare but salient examples, or emotional experiences (e.g., an electric vehicle (EV) battery explosion), they may overweight the likelihood of such events occurring in the future. In particular, if a single event is repeatedly portrayed in the media, individuals may think that such an event occurs more often than they actually occur in reality. In addition, if a single salient but rare event happens to a particular individual (e.g., an EV battery explosion), that individual may overweight the likelihood of a similar event occurring in the future.

Unfortunately, people may overweight the importance of salient events and may have excessive fear or anxiety about a similar, salient event occurring in the future that is disproportionate to its actual likelihood of occurrence. Some aspects of the present disclosure are directed to a method for protecting people from inappropriately overweighting information. Some aspects of the present disclosure ameliorate overweighting the importance of salient events using a machine learning model trained on a set of past overweight events from the user as well as the broader population to provide an intervention strategy for protecting the user from inappropriately overweighting salient events.

Figure 3:
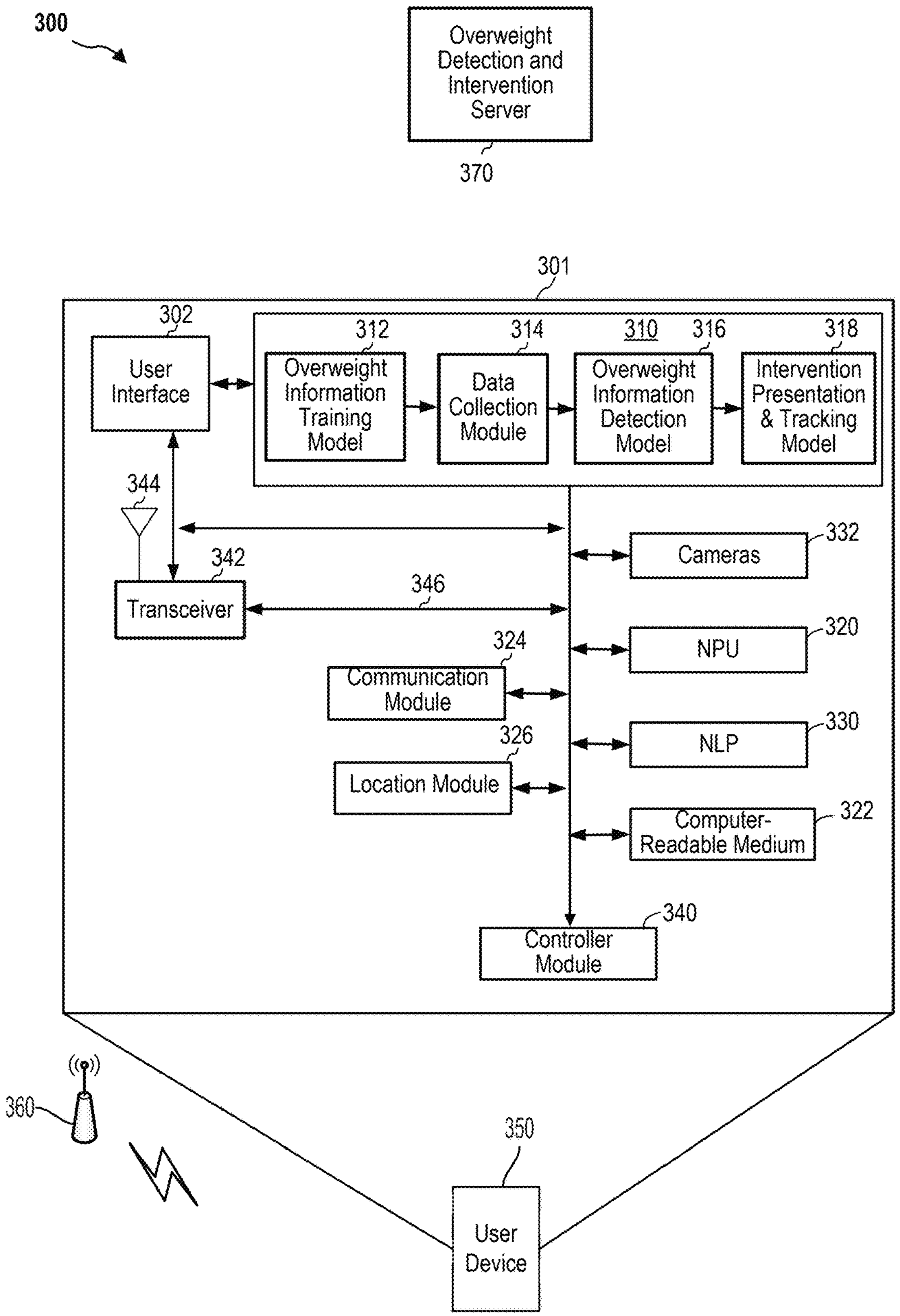
FIG. 3 is a diagram illustrating a hardware implementation for an information overweight detection and intervention system, according to aspects of the present disclosure.

FIG. 3 is a diagram illustrating a hardware implementation for an information overweight detection and intervention system 300, according to aspects of the present disclosure. The information overweight detection and intervention system 300 may be configured to train a statistical model to classify salient information that may be overweight by individuals to provide a trained statistical model. The information overweight detection and intervention system 300 is also configured to collect data from a user about salient information experienced by the user or to which the user is exposed. In response, the information overweight detection and intervention system 300 is configured to analyze the salient information using the trained statistical model to identify and classify salient information that the user may overweight to identify overweight information. In addition, the information overweight detection and intervention system 300 is configured to present one or more interventions to the user to prevent the user from overweighting the identified overweight information.

The information overweight detection and intervention system 300 includes a user monitoring system 301 and an overweight detection and intervention server 370, in this aspect of the present disclosure. The user monitoring system 301 may be a component of a user device 350. The user device 350 may be a cellular phone (e.g., a smart phone), a personal digital assistant (PDA), a wireless modem, a wireless communications device, a handheld device, a laptop computer, a cordless phone, a wireless local loop (WLL) station, a tablet, a camera, a gaming device, a netbook, a smartbook, an ultrabook, a medical device or equipment, biometric sensors/devices, wearable devices (e.g., smart watches, smart clothing, smart glasses, smart wrist bands, smart jewelry (e.g., smart ring, smart bracelet)), an entertainment device (e.g., a music or video device, or a satellite radio), a global positioning system device, or any other suitable device that is configured to communicate via a wireless or wired medium. For example, the user device may be an autonomous vehicle, a semi-autonomous vehicle, or a vehicle including an advanced driver assistance system configured to capture video regarding events witnessed by a driver to detect overweight events. The overweight event may be detected by monitoring vital signs of the user during operation of the autonomous vehicle using a biometric signals captured for the user when experiencing a salient event.

The overweight detection and intervention server 370 may connect to the user device 350 for providing an intervention in response to detecting overweight information by the user. For example, the overweight detection and intervention server 370 may suggest interventions to prevent the user from overweighting salient events based on a classification of each event. For example, suggested interventions may include presenting actual statistical data about the type of event, instructing the individual on how to avoid situations that raise fear or anxiety, and the like. The interventions may be presented to the user and the system may then track the user's reactions to the interventions and continuously revise the suggested interventions.

The user monitoring system 301 may be implemented with an interconnected architecture, represented generally by an interconnect 346. The interconnect 346 may include any number of point-to-point interconnects, buses, and/or bridges depending on the specific application of the user monitoring system 301 and the overall design constraints. The interconnect 346 links together various circuits including one or more processors and/or hardware modules, represented by a user interface 302, a user activity module 310, a neutral network processor (NPU) 320, a computer-readable medium 322, a communication module 324, a location module 326, a natural language processor (NLP) 330, cameras 332, and a controller module 340. The interconnect 346 may also link various other circuits such as timing sources, peripherals, voltage regulators, and power management circuits, which are well known in the art, and, therefore, will not be described any further.

The user monitoring system 301 includes a transceiver 342 coupled to the user interface 302, the user activity module 310, the NPU 320, the computer-readable medium 322, the communication module 324, the location module 326, the NLP 330, the cameras 332, and the controller module 340. The transceiver 342 is coupled to an antenna 344. The transceiver 342 communicates with various other devices over a transmission medium. For example, the transceiver 342 may receive commands via transmissions from a user or a connected device. In this example, the transceiver 342 may receive/transmit information for the user activity module 310 to/from connected devices within the vicinity of the user device 350.

The user monitoring system 301 includes the NPU 320 coupled to the computer-readable medium 322. The NPU 320 performs processing, including the execution of software stored on the computer-readable medium 322 to provide a neural network model for user monitoring and intervention in response to overweight detection functionality according to the present disclosure. The software, when executed by the NPU 320, causes the user monitoring system 301 to perform the various functions described for information overweight detection and intervention through the user device 350, or any of the modules (e.g., 310, 324, 326, 330, 332, and/or 340). The computer-readable medium 322 may also be used for storing data that is manipulated by the NLP 330 when executing the software to analyze convent or events viewed by the user, as captured by a first camera (fixed on the user) and a second camera fixed on the user's environment.

The location module 326 may determine a location of the user device 350. For example, the location module 326 may use a global positioning system (GPS) to determine the location of the user device 350. The location module 326 may implement a dedicated short-range communication (DSRC)-compliant GPS unit. A DSRC-compliant GPS unit includes hardware and software to make the autonomous vehicle 350 and/or the location module 326 compliant with the following DSRC standards, including any derivative or fork thereof: EN 12253:2004 Dedicated Short-Range Communication-Physical layer using microwave at 5.8 GHz (review); EN 12795:2002 Dedicated Short-Range Communication (DSRC)—DSRC Data link layer: Medium Access and Logical Link Control (review); EN 12834:2002 Dedicated Short-Range Communication—Application layer (review); EN 13372:2004 Dedicated Short-Range Communication (DSRC)—DSRC profiles for RTTT applications (review); and EN ISO 14906:2004 Electronic Fee Collection—Application interface.

The communication module 324 may facilitate communications via the transceiver 342. For example, the communication module 324 may be configured to provide communication capabilities via different wireless protocols, such as 5G new radio (NR), Wi-Fi, long term evolution (LTE), 4G, 3G, etc. The communication module 324 may also communicate with other components of the user device 350 that are not modules of the user monitoring system 301. The transceiver 342 may be a communications channel through a network access point 360. The communications channel may include DSRC, LTE, LTE-D2D, mmWave, Wi-Fi (infrastructure mode), Wi-Fi (ad-hoc mode), visible light communication, TV white space communication, satellite communication, full-duplex wireless communications, or any other wireless communications protocol such as those mentioned herein.

The user monitoring system 301 also includes the NLP 330 to receive and analyze language and content viewed by the user communications to determine the user's physical or emotional status in response to the viewed content. For example, the user's physical or emotional status may indicate overweight of the viewed content. In some aspects of the present disclosure, the user monitoring system 301 may use natural language processing of the NLP 330 to extract terms from overweight content viewed by the user, such as terms revealing that the user is exhibiting a significant reaction to the viewed content. The NLP 330 may receive and analyze overweight content viewed by the user to determine the user's concerns around the overweight content view by the user.

The user activity module 310 may be in communication with the user interface 302, the NPU 320, the computer-readable medium 322, the communication module 324, the location module 326, the NLP 330, the controller module 340, and the transceiver 342. In one configuration, the user activity module 310 monitors viewed content from the user interface 302. The user interface 302 may monitor content viewed by the user to and from the communication module 324. According to aspects of the present disclosure, the NLP 330 may use natural language processing to extract terms regarding viewed content, such as terms revealing that the user is a strong reaction to the viewed content (e.g., overweight viewed content).

As shown in FIG. 3, the user activity module 310 includes an overweight information training module 312, a data collection module 314, an overweight information detection model 316, and an intervention presentation and tracking model 318. The overweight information training module 312, the data collection module 314, the overweight information detection model 316, and the intervention presentation and tracking model 318 may be components of a same or different artificial neural network, such as a deep convolutional neural network (CNN). The user activity module 310 is not limited to a CNN. The user activity module 310 monitors and analyzes content viewed by the user through the user interface 302 or during user navigation, such as when the user device 350 is an autonomous, semi-autonomous vehicle, or an advanced driver assistance system (ADAS) is included in a vehicle operated by the user.

Figure 4:
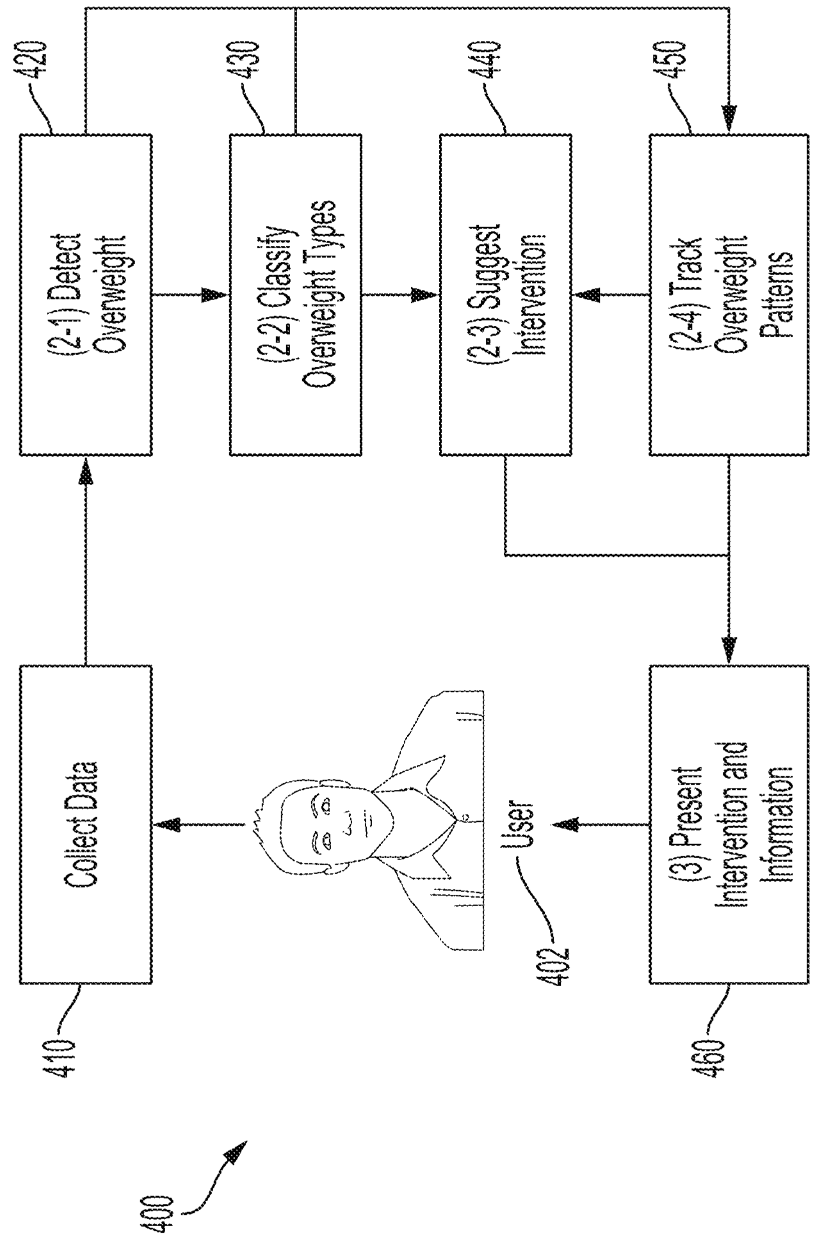
FIG. 4 is a block diagram illustrating an information overweight detection and intervention system, in accordance with aspects of the present disclosure.

This configuration of the user activity module 310 includes the overweight information training module 312 for training a statistical model to classify salient information that may be overweight by individuals to provide a trained statistical model. The user activity module 310 also includes the data collection module 314 for collecting data from a user about salient information experienced by the user or to which the user is exposed. The user activity module 310 also includes the overweight information training module 312 for analyzing the salient information using the trained statistical model to identify and classify salient information that the user may overweight to identify overweight information. The user activity module 310 further includes the intervention presentation and tracking model 318 for presenting one or more interventions to the user to prevent the user from overweighting the identified overweight information, for example, as shown in FIG. 4. In some aspects of the present disclosure, the intervention presentation and tracking model 318 may be implemented and/or work in conjunction with the overweight detection and intervention server 370.

FIG. 4 is a block diagram illustrating an information overweight detection and intervention system 400, in accordance with aspects of the present disclosure. In some aspects of the present disclosure, the information overweight detection and intervention system 400 relies on a trained statistical model to classify salient information that may be overweight by individuals. The information overweight detection and intervention system 400 collects data from a user about salient information experienced by a user or to which the user is exposed. Once captured, the salient information is analyzed using the trained statistical model to identify and classify salient information that the user may overweight to identify overweight information. Once detected, the information overweight detection and intervention system 400 presents one or more interventions to the user to prevent the user from overweighting the identified overweight information.

In this configuration, the information overweight detection and intervention system 400 includes a user 402, a data collection component 410, an overweight detection component 420, an overweight type classification component 430, an intervention suggestion component 440, an overweight pattern tracing component 450, and an intervention presentation component 460. In some aspects of the present disclosure, the data collection component 410 collects both past and active data sensitive to a subject's perceived overweight several approaches. For example, data collection may be performed using self-reporting from the user 402, a browsing history of the user 402, physiological signals of the user 402, video, and speech of the user 402. In addition, the overweight detection component 420 may detect overweighting with different types, which may correspond to a specific intervention strategy.

In some aspects of the present disclosure, the overweight type classification component 430 may be a subcomponent of the overweight detection component 420. In some aspects of the present disclosure, the overweight detection component 420 is configured to detect overweighting by aggregating the data collected in the data collection component 410, and the statistical models trained using the user's past overweight data and/or overweight data collected from a broader population. The overweight type classification component 430 may be a subcomponent of the overweight detection component 420 for determining the type of overweight, such as a statistical overweight and/or an emotional overweight. In some aspects of the present disclosure, the overweight type classification component 430 determines the type of overweight using a supervised or unsupervised model.

According to this aspect of the present disclosure, the intervention suggestion component 440 is configured as a subcomponent of the information overweight detection and intervention system 400. For example, the intervention suggestion component 440 is configured for suggesting interventions in response to detection of overweight information by the user. In this example, the suggested interventions include presenting a comprehensive comparison, or instructing how to avoid situations that cause fear to address different types of overweight. In addition, the overweight pattern tracing component 450 may be a subcomponent for tracking the perceived overweight continuously and revising the suggested interventions. In some aspects of the present disclosure, the intervention presentation component 460 displays the information about the interventions and the changes of the perceived overweight that may be used for supporting communication, awareness, and transparency of the information overweight detection and intervention system 400.

Figure 5:
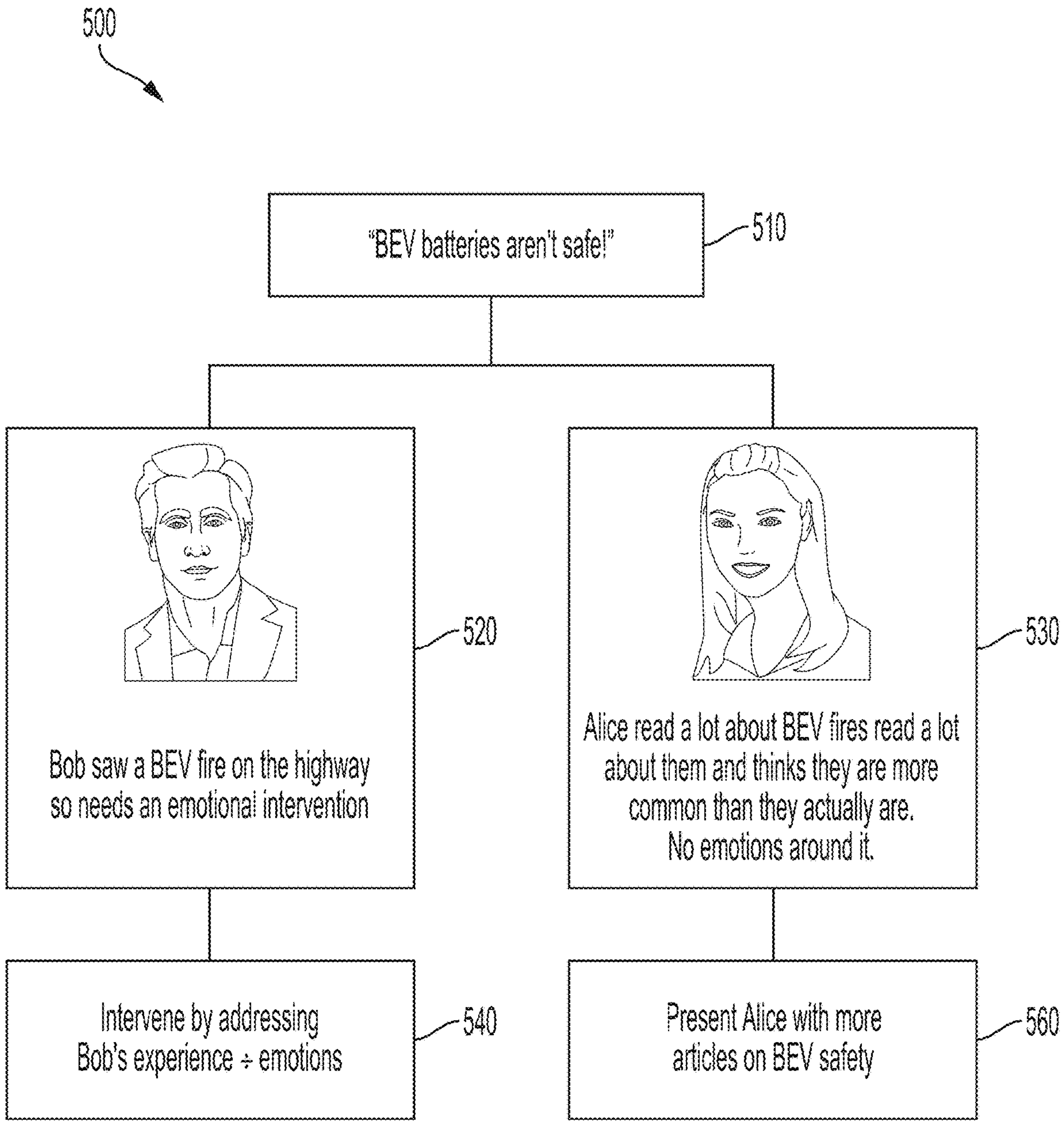
FIG. 5 is a block diagram illustrating detection and intervention in response to detection of overweight information by a user, according to aspects of the present disclosure.

FIG. 5 is a block diagram illustrating an overweight detection and intervention process 500 in response to detection of overweight information by a user, according to aspects of the present disclosure. In this example, two individuals (e.g., Bob and Alice) view a content 510, causing both Bob and Alice to believe battery elective vehicle (BEV) batteries are not safe due to overweight of such information. The content 510 may be viewed online, in a periodical, or seen in real life. For example, as shown in block 520, Bob witnesses a BEV fire on the highway during operation of a vehicle. In some aspects of the present disclosure, a camera of the user vehicle captures the BEV fire on the highway and a driver facing camera captures a reaction of the user while witnessing the BEV fire during operation of the vehicle. In this example, Bob's overweight of the BEV fire is classified as an emotional overweight, so an emotional intervention is provided at block 540. The emotional intervention may be determined by the intervention suggestion component 440, which is a subcomponent of the information overweight detection and intervention system 400 of FIG. 4.

At block 530, Alice reads a significant amount of content regarding BEV and overweight of BEV fires leads Alice to believe that BEV fires are very common, although BEV fires are actually quite uncommon. In this example, Alice's overweight of BEV fires is identified as a statistical overweight, as Alice's feelings are not involved. At block 560, Alice is provided with more articles on BEV safety. In these aspects of the present disclosure, the overweight detection and intervention process 500 may use natural language processing (e.g., the NLP 330 of FIG. 3) to extract terms from the content viewed by Alice, in which the terms reveal that the BEV fires may be overweight by Alice. In addition, classification of the information overweight may be performed by the overweight type classification component 430 of overweight detection component 420 for determining the type of overweight, such as a statistical overweight and/or an emotional overweight. In these aspects of the present disclosure, the overweight type classification component 430 determines the type of overweight using a supervised or unsupervised model, as shown in FIG. 4. The information overweight and intervention process 500 may engage in a process, for example, as shown in FIG. 6.

Figure 6:
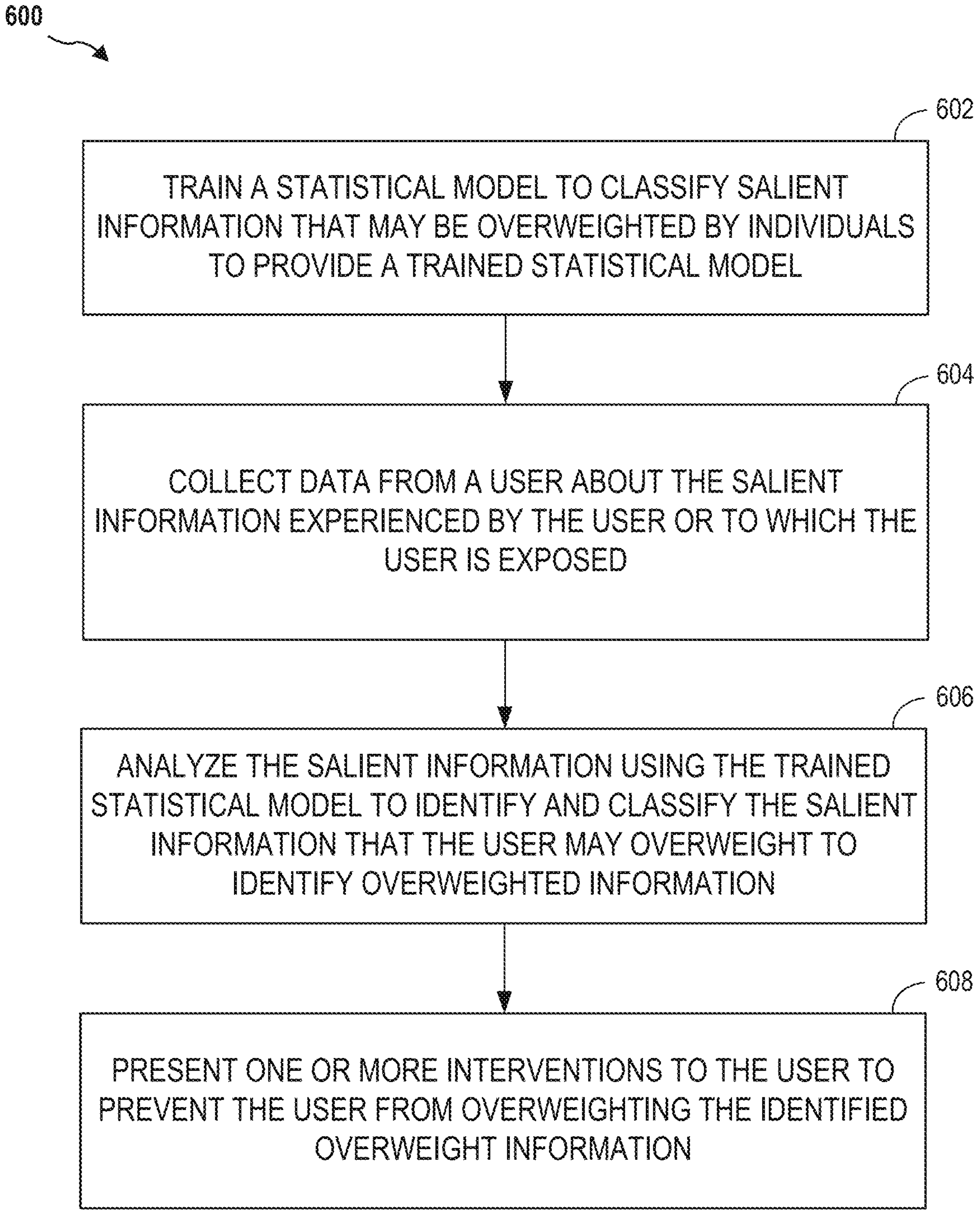
FIG. 6 is a flowchart illustrating a method for information overweight detection and intervention, according to aspects of the present disclosure.

FIG. 6 is a flowchart illustrating a method for information overweight detection and intervention, according to aspects of the present disclosure. A method 600 of FIG. 6 begins at block 602, in which a statistical model is trained to classify salient information that may be overweight by individuals to provide a trained statistical model. For example, as described in FIG. 3, this configuration of the user activity module 310 includes the overweight information training module 312 for training a statistical model to classify salient information that may be overweight by individuals to provide a trained statistical model.

As shown in FIG. 4, the information overweight detection and intervention system 400 relies on a trained statistical model to classify salient information that may be overweight by individuals. The statistical model may be trained to determine the type of overweighting likely to occur using either supervised learning (e.g., based on collected data from the population) or unsupervised learning. In some aspects of the present disclosure, the information overweight detection and intervention system 400 protects individuals from inappropriately overweighting information. The information overweight detection and intervention system 400 may collect data of events that an individual may potentially overweight. The data may be collected by a variety of means including user self-reporting, user browser history, physiological signals (e.g., heart rate), video, and speech captured from the user. The information overweight detection and intervention system 400 may then aggregate the collected data from the individual and from the broader population using the NPU 320.

Referring again to FIG. 6, at block 604, data is collected from a user about salient information experienced by the user or to which the user is exposed For example, as shown in FIG. 3, the user activity module 310 also includes the data collection module 314 for collecting data from a user about salient information experienced by the user or to which the user is exposed. As shown in FIG. 4, the data collection component 410 collects both past and active data sensitive to a subject's perceived overweight several approaches. For example, data collection may be performed using self-reporting from the user 402, a browsing history of the user 402, physiological signals of the user 402, video, and speech of the user 402. As shown in FIG. 5, at block 530, data is collected indicating that Alice reads a significant amount of content regarding BEV, and overweight of BEV fires leads Alice to believe that BEV fires are very common, although BEV fires are actually quire uncommon.

At block 606, the salient information using the trained statistical model is analyzed to identify and classify salient information that the user may overweight to identify overweight information. For example, as shown in FIG. 3, the user activity module 310 also includes the overweight information training module 312 for analyzing the salient information using the trained statistical model to identify and classify salient information that the user may overweight to identify overweight information. As shown in FIG. 4, the overweight detection component 420 is configured to detect overweight by aggregating the data collected in the data collection component 410 and the statistical models trained using the user's past overweight data and/or overweight data collected from a broader population. The overweight type classification component 430 may be a subcomponent of overweight detection component 420 for determining the type of overweight, such as a statistical overweight and/or an emotional overweight. In some aspects of the present disclosure, the overweight type classification component 430 determines the type of overweight using a supervised or unsupervised model.

At block 608, one or more interventions are presented to the user to prevent the user from overweighting the identified overweight information. For example, as shown in FIG. 3, the user activity module 310 further includes the intervention presentation and tracking model 318 for presenting one or more interventions to the user to prevent the user from overweighting the identified overweight information. As shown in FIG. 4, the intervention presentation component 460 displays the information about the interventions and the changes of the perceived overweight that may be used for supporting communication, awareness, and transparency of the information overweight detection and intervention system 400. The intervention presentation component 460 may suggest interventions to prevent the individual from overweighting the events based on the classification of each event. Interventions may include presenting actual statistical data about the type of event, instructing the individual on how to avoid situations that raise fear or anxiety, and the like, for example, as shown in FIG. 5. The interventions may be presented to the user and the information overweight detection and intervention system 400 may then track the user's reactions to the interventions and continuously revise the suggested interventions.

The method 600 further includes analyzing the salient information by aggregating data collected from the user and overweight information predicted from the trained statistical model. The method 600 also includes collecting data by collecting a past data and an active data corresponding to a perceived overweight of the user. The method 600 further includes collecting data by receiving self-reports from the user, and/or analyzing a browsing history of the user. The method 600 also includes collecting data by collecting a psychological data and/or a biological data while the user is exposed to the salient information. The method 600 further includes detecting overweighting of statistical data based on at least a heart rate of the user, according to biological data measured from the user.

Aspects of the present disclosure are directed to a compromised decision monitoring and recommendation system. In some aspects of the present disclosure, the compromised decision monitoring and recommendation system logs an initial decision-making process to analyze and understand a current state of events. The compromised decision monitoring and recommendation system is configured to process an initial decision-making process to analyze and understand the current state of events. This process enables the compromised decision monitoring and recommendation system to show how past decisions led to a current state of events for addressing potential remorse. In some aspects of the present disclosure, the compromised decision monitoring and recommendation system provides advice using a trained machine learning model to reduce the impact of future compromises associated with a compromised decision.

The various operations of methods described above may be performed by any suitable means capable of performing the corresponding functions. The means may include various hardware and/or software component(s) and/or module (s), including, but not limited to, a circuit, an application-specific integrated circuit (ASIC), or processor. Generally, where there are operations illustrated in the figures, those operations may have corresponding counterpart means-plus-function components with similar numbering.

As used herein, the term "determining" encompasses a wide variety of actions. For example, "determining" may include calculating, computing, processing, deriving, investigating, looking up (e.g., looking up in a table, a database or another data structure), ascertaining, and the like. Additionally, "determining" may include receiving (e.g., receiving information), accessing (e.g., accessing data in a memory), and the like. Furthermore, "determining" may include resolving, selecting, choosing, establishing, and the like.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logical blocks, modules and circuits described in connection with the present disclosure may be implemented or performed with a processor configured according to the present disclosure, a digital signal processor (DSP), an ASIC, a field-programmable gate array signal (FPGA) or other programmable logic device (PLD), discrete gate or transistor logic, discrete hardware components, or any combination thereof designed to perform the functions described herein. The processor may be a microprocessor, but, in the alternative, the processor may be any commercially available processor, controller, microcontroller, or state machine specially configured as described herein. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the present disclosure may be embodied directly in hardware, in a software module executed by a processor, or in a combination of the two. A software module may reside in any form of storage medium that is known in the art. Some examples of storage media that may be used include random access memory (RAM), read-only memory (ROM), flash memory, erasable programmable read-only memory (EPROM), electrically erasable programmable read-only memory (EEPROM), registers, a hard disk, a removable disk, a CD-ROM, and so forth. A software module may comprise a single instruction, or many instructions, and may be distributed over several different code segments, among different programs, and across multiple storage media. A storage medium may be coupled to a processor such that the processor can read information from, and write information to, the storage medium. In the alternative, the storage medium may be integral to the processor.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

The functions described may be implemented in hardware, software, firmware, or any combination thereof. If implemented in hardware, an example hardware configuration may comprise a processing system in a device. The processing system may be implemented with a bus architecture. The bus may include any number of interconnecting buses and bridges depending on the specific application of the processing system and the overall design constraints. The bus may link together various circuits including a processor, machine-readable media, and a bus interface. The bus interface may connect a network adapter, among other things, to the processing system via the bus. The network adapter may implement signal processing functions. For certain aspects, a user interface (e.g., keypad, display, mouse, joystick, etc.) may also be connected to the bus. The bus may also link various other circuits such as timing sources, peripherals, voltage regulators, power management circuits, and the like, which are well known in the art, and therefore, will not be described any further.

The processor may be responsible for managing the bus and processing, including the execution of software stored on the machine-readable media. Examples of processors that may be specially configured according to the present disclosure include microprocessors, microcontrollers, DSP processors, and other circuitry that can execute software. Software shall be construed broadly to mean instructions, data, or any combination thereof, whether referred to as software, firmware, middleware, microcode, hardware description language, or otherwise. Machine-readable media may include, by way of example, RAM, flash memory, ROM, programmable read-only memory (PROM), EPROM, EEPROM, registers, magnetic disks, optical disks, hard drives, or any other suitable storage medium, or any combination thereof. The machine-readable media may be embodied in a computer-program product. The computer-program product may comprise packaging materials.

In a hardware implementation, the machine-readable media may be part of the processing system separate from the processor. However, as those skilled in the art will readily appreciate, the machine-readable media, or any portion thereof, may be external to the processing system. By way of example, the machine-readable media may include a transmission line, a carrier wave modulated by data, and/or a computer product separate from the device, all which may be accessed by the processor through the bus interface. Alternatively, or in addition, the machine-readable media, or any portion thereof, may be integrated into the processor, such as the case may be with cache and/or specialized register files. Although the various components discussed may be described as having a specific location, such as a local component, they may also be configured in various ways, such as certain components being configured as part of a distributed computing system.

The processing system may be configured with one or more microprocessors providing the processor functionality and external memory providing at least a portion of the machine-readable media, all linked together with other supporting circuitry through an external bus architecture. Alternatively, the processing system may comprise one or more neuromorphic processors for implementing the neuron models and models of neural systems described herein. As another alternative, the processing system may be implemented with an ASIC with the processor, the bus interface, the user interface, supporting circuitry, and at least a portion of the machine-readable media integrated into a single chip, or with one or more FPGAs, PLDs, controllers, state machines, gated logic, discrete hardware components, or any other suitable circuitry, or any combination of circuits that can perform the various functions described throughout this present disclosure. Those skilled in the art will recognize how best to implement the described functionality for the processing system depending on the particular application and the overall design constraints imposed on the overall system.

The machine-readable media may comprise a number of software modules. The software modules include instructions that, when executed by the processor, cause the processing system to perform various functions. The software modules may include a transmission module and a receiving module. Each software module may reside in a single storage device or be distributed across multiple storage devices. By way of example, a software module may be loaded into RAM from a hard drive when a triggering event occurs. During execution of the software module, the processor may load some of the instructions into cache to increase access speed. One or more cache lines may then be loaded into a special purpose register file for execution by the processor. When referring to the functionality of a software module below, it will be understood that such functionality is implemented by the processor when executing instructions from that software module. Furthermore, it should be appreciated that aspects of the present disclosure result in improvements to the functioning of the processor, computer, machine, or other system implementing such aspects.

If implemented in software, the functions may be stored or transmitted over as one or more instructions or code on a non-transitory computer-readable medium. Computer-readable media include both computer storage media and communication media, including any medium that facilitates transfer of a computer program from one place to another. A storage medium may be any available medium that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Additionally, any connection is properly termed a computer-readable medium. For example, if the software is transmitted from a website, server, or other remote source using a coaxial cable, fiber optic cable, twisted pair, digital subscriber line (DSL), or wireless technologies such as infrared (IR), radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk, and Blu-ray® disc where disks usually reproduce data magnetically, while discs reproduce data optically with lasers. Thus, in some aspects computer-readable media may comprise non-transitory computer-readable media (e.g., tangible media). In addition, for other aspects, computer-readable media may comprise transitory computer-readable media (e.g., a signal). Combinations of the above should also be included within the scope of computer-readable media.

Thus, certain aspects may comprise a computer program product for performing the operations presented herein. For example, such a computer program product may comprise a computer-readable medium having instructions stored (and/or encoded) thereon, the instructions being executable by one or more processors to perform the operations described herein. For certain aspects, the computer program product may include packaging material.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a CD or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes, and variations may be made in the arrangement, operation, and details of the methods and apparatus described above without departing from the scope of the claims.

What is claimed is:

1. A method for information overweigh detection and intervention, the method comprising:

training, by a server computer, a statistical model to classify salient information regarding events experienced by individuals or to which the individuals are exposed, in which a likelihood of a reoccurrence of the events may be overweighed by the individuals to provide a trained statistical model;

collecting, from a user device, data from a user about the salient information regarding events experienced by the user or to which the user is exposed, wherein the user device comprises a neural network processor, a natural language processor, and one or more cameras, and wherein collecting the data comprises processing at least one of video and speech of the user via the neural network processor, the natural language processor, and the one or more cameras;

analyzing, by the server computer, the salient information using the trained statistical model to classify the salient information and predict an event experienced by the user or to which the user is exposed, in which a likelihood of a reoccurrence of the identified event may be overweighed by the user, wherein analyzing further comprises determining a type of overweigh comprising a statistical overweigh and an emotional overweigh;

presenting, by the user device, one or more interventions to the user to prevent the user from overweighing the likelihood of the reoccurrence of the identified event; and tracking, by an intervention tracking model on the user device, user reactions to the one or more interventions to update the trained statistical model on the server computer.

2. The method of claim 1, in which analyzing the salient information comprises aggregating data collected from the user and overweighed information predicted from the trained statistical model.

3. The method of claim 1, which further comprises updating the trained statistical model according to the identified overweighed information using supervised or unsupervised learning.

4. The method of claim 1, in which the collecting data comprises collecting a past data and an active data corresponding to a perceived overweigh of the user.

5. The method of claim 1, in which the collecting data comprises receiving self-reports from the user, and/or analyzing a browsing history of the user.

6. The method of claim 1, in which the collecting data further comprises:

collecting a psychological data and/or a biological data while the user is exposed to the salient information; and detecting overweighing of statistical data based on at least a heart rate of the user.

7. The method of claim 1, in which tracking comprises:

continuously tracking the identified overweighed information; and updating the trained statistical model to refine the one or more interventions based on the continuously tracking.

8. The method of claim 1, in which presenting comprises:

detecting changes of the identified overweighed information for supporting communication, awareness, and transparency of the one or more interventions; and displaying changes of the identified overweighed information and the one or more interventions.

9. A non-transitory computer-readable medium having program code recorded thereon for information overweigh detection and intervention, the program code being executed by a processor and comprising:

program code to train a statistical model to classify salient information regarding events experienced by individuals or to which the individuals are exposed, in which a likelihood of a reoccurrence of the events may be overweighed by the individuals to provide a trained statistical model;

program code to collect data from a user about the salient information regarding events experienced by the user or to which the user is exposed, wherein the user device comprises a neural network processor, a natural language processor, and one or more cameras, and wherein the program code to collect the data comprises processing at least one of video and speech of the user via the neural network processor, the natural language processor, and the one or more cameras;

program code to analyze the salient information using the trained statistical model to classify the salient information and identify an event experienced by the user or to which the user is exposed, in which a likelihood of a reoccurrence of the identified event may be overweighed by the user, wherein the program code to analyze further comprises program code to determine a type of overweigh comprising a statistical overweigh and an emotional overweigh;

program code to present one or more interventions to the user to prevent the user from overweighing the likelihood of the reoccurrence of the identified event; and tracking, by an intervention tracking model on the user device, user reactions to the one or more interventions to update the trained statistical model on the server computer.

10. The non-transitory computer-readable medium of claim 9, in which the program code to analyze the salient information comprises program code to aggregate data collected from the user and overweighed information predicted from the trained statistical model.

11. The non-transitory computer-readable medium of claim 9, further comprising updating the trained statistical model according to the identified overweighed information using supervised or unsupervised learning.

12. The non-transitory computer-readable medium of claim 9, in which the program code to collect data comprises collecting a past data and an active data corresponding to a perceived overweigh of the user.

13. The non-transitory computer-readable medium of claim 9, in which the program code to collect data comprises program code to receive self-reports from the user, and/or analyzing a browsing history of the user.

14. The non-transitory computer-readable medium of claim 9, in which the program code to collect further comprises:

program code to collect a psychological data and/or a biological data while the user is exposed to the salient information; and program code to detect overweighing of statistical data based on at least a heart rate of the user.

15. The non-transitory computer-readable medium of claim 9, in which program code to track comprises:

program code to continuously track the identified overweighed information; and program code to update the trained statistical model to refine the one or more interventions based on the continuously tracking.

16. The non-transitory computer-readable medium of claim 9, in which the program code to present comprises:

program code to detect changes of the identified overweighed information for supporting communication, awareness, and transparency of the one or more interventions; and program code to display changes of the identified overweighed information and the one or more interventions.

17. A system for information overweigh detection and intervention, the system comprising:

an overweigh information training module to train a statistical model, on a server computer, to classify salient information regarding events experienced by individuals or to which the individuals are exposed, in which a likelihood of a reoccurrence of the events may be overweighed by the individuals to provide a trained statistical model;

a data collection module to collect data from a user about the salient information regarding events experienced by the user or to which the user is exposed, wherein the user device comprises a neural network processor, a natural language processor, and one or more cameras, and wherein to collect the data comprises processing at least one of video and speech of the user via the neural network processor, the natural language processor, and the one or more cameras;

an overweighed information detection model to analyze the salient information using the trained statistical model to classify the salient information and identify an event experienced by the user or to which the user is exposed, in which a likelihood of a reoccurrence of the identified event may be overweighed by the user, wherein to analyze further comprises to determine a type of overweigh comprising a statistical overweigh and an emotional overweigh; and an intervention presentation and tracking model to present one or more interventions to the user to prevent the user from overweighing the likelihood of the reoccurrence of the identified event and to track user reactions to the one or more interventions to update the trained statistical model on the server computer.

18. The system of claim 17, in which the overweighed information detection model is further to aggregate data collected from the user and overweighed information predicted from the trained statistical model.

19. The system of claim 17, in which the intervention presentation and tracking model is further to continuously track the identified overweighed information, and to update the trained statistical model to refine the one or more interventions based on the continuously tracking.

20. The system of claim 17, in which the intervention presentation and tracking model is further to detect changes of the identified overweighed information for supporting communication, awareness, and transparency of the one or more interventions, and to display changes of the identified overweighed information and the one or more interventions.

* * * * *